United States Patent
Okamoto et al.

(10) Patent No.: US 11,931,499 B2
(45) Date of Patent: Mar. 19, 2024

(54) PRESSURE DETECTOR

(71) Applicant: Nikkiso Company Limited, Tokyo (JP)

(72) Inventors: Shingo Okamoto, Shizuoka (JP); Hiroyuki Kawajiri, Shizuoka (JP); Ryo Kato, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 748 days.

(21) Appl. No.: 17/093,821

(22) Filed: Nov. 10, 2020

(65) Prior Publication Data
US 2021/0052801 A1 Feb. 25, 2021

Related U.S. Application Data

(63) Continuation of application No. PCT/JP2019/019394, filed on May 15, 2019.

(30) Foreign Application Priority Data

May 16, 2018 (JP) ................................. 2018-094463

(51) Int. Cl.
*A61M 1/36* (2006.01)
*A61M 1/16* (2006.01)

(52) U.S. Cl.
CPC ........ *A61M 1/3639* (2013.01); *A61M 1/1601* (2014.02); *A61M 1/3607* (2014.02); *A61M 2205/3344* (2013.01)

(58) Field of Classification Search
CPC .............. A61M 1/3639; A61M 1/1601; A61M 1/3607; A61M 2205/3344; A61M 1/3641;
(Continued)

(56) References Cited

U.S. PATENT DOCUMENTS 4,908,493 A 3/1990 Susemihl
5,221,271 A 6/1993 Nicholson et al.
(Continued)

FOREIGN PATENT DOCUMENTS

DE 102008034920 A1 9/2009
EP 0074733 A1 3/1983
(Continued)

OTHER PUBLICATIONS

European Search Report for Application No. 19803045.4, dated Dec. 13, 2021.
(Continued)

*Primary Examiner* — Freddie Kirkland, III
(74) *Attorney, Agent, or Firm* — Young Basile Hanlon & MacFarlane, P.C.

(57) ABSTRACT

A pressure detector including a case connectable to a flow route and attachable to a predetermined attaching surface; and a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion. The pressure detector includes an inlet port including a connecting portion connectable to the flow route, and a flow-route portion through which the liquid flows into an inlet opening of the liquid-phase portion; and an outlet port including a connecting portion connectable to the flow route, and a flow-route portion through which the liquid having flowed into the liquid-phase portion is discharged from an outlet opening. The outlet opening is positioned in a part of the liquid-phase portion that includes a highest point in a (Continued)

vertical direction in a state where the case is attached to the predetermined attaching surface, and the outlet port extends obliquely upward from the outlet opening.

11 Claims, 10 Drawing Sheets

(58) Field of Classification Search
CPC . G01L 7/082; G01L 19/0023; G01L 19/0038; G01L 19/143
See application file for complete search history.

(56) References Cited

U.S. PATENT DOCUMENTS

| | | | |
|---|---|---|---|
| 5,722,946 | A | 3/1998 | Mudloff et al. |
| 6,392,208 | B1 | 5/2002 | Arx |
| 7,493,824 | B2* | 2/2009 | Brucksch ............ A61M 1/3639 |
| | | | 73/756 |
| 8,092,414 | B2 | 1/2012 | Schnell et al. |
| 8,113,060 | B2* | 2/2012 | Jonsson ............... A61M 1/3641 |
| | | | 73/756 |
| 8,960,010 | B1 | 2/2015 | Crnkovich et al. |
| 10,300,190 | B2* | 5/2019 | Stuva ................. A61M 1/36224 |
| 10,775,252 | B2 | 9/2020 | Funamura et al. |
| 11,478,885 | B2* | 10/2022 | Okamoto ................. G01L 19/06 |
| 11,554,202 | B2* | 1/2023 | Koda ......................... A61M 1/85 |
| 2003/0115965 | A1 | 6/2003 | Mittelstein et al. |
| 2004/0050168 | A1 | 3/2004 | Uberreiter |
| 2007/0118153 | A1 | 5/2007 | Funamura et al. |
| 2007/0234817 | A1* | 10/2007 | Brucksch ............ A61M 1/3639 |
| | | | 73/756 |
| 2007/0295093 | A1 | 12/2007 | Reiter et al. |
| 2009/0071258 | A1 | 3/2009 | Kouda et al. |
| 2010/0018317 | A1 | 1/2010 | Kitani et al. |
| 2010/0186518 | A1 | 7/2010 | Jonsson et al. |
| 2011/0290352 | A1 | 12/2011 | Reiter et al. |
| 2015/0306299 | A1 | 10/2015 | Stuva et al. |
| 2017/0312412 | A1 | 11/2017 | Mochizuki |
| 2017/0340798 | A1 | 11/2017 | Lindley et al. |
| 2018/0080843 | A1* | 3/2018 | Funamura ............ G01L 19/0046 |
| 2018/0093033 | A1* | 4/2018 | Crnkovich .......... A61M 1/3639 |
| 2019/0336673 | A1* | 11/2019 | Crnkovich .......... A61M 1/3403 |
| 2020/0198459 | A1 | 6/2020 | Bouffier et al. |
| 2020/0338254 | A1* | 10/2020 | Maki ...................... G01L 27/002 |
| 2021/0052796 | A1* | 2/2021 | Kawajiri ............. G01L 19/0023 |
| 2021/0052797 | A1* | 2/2021 | Kawajiri .................... G01L 7/08 |
| 2021/0052800 | A1* | 2/2021 | Okamoto ............ G01L 19/0038 |
| 2021/0052801 | A1* | 2/2021 | Okamoto ............ A61M 1/3607 |
| 2021/0106744 | A1 | 4/2021 | Okamoto et al. |
| 2021/0107100 | A1* | 4/2021 | Okamoto ............ A61M 1/3641 |
| 2022/0016327 | A1* | 1/2022 | Ito ....................... A61M 1/3641 |

FOREIGN PATENT DOCUMENTS

| | | |
|---|---|---|
| EP | 0330891 A1 | 9/1989 |
| EP | 1843140 A2 | 10/2007 |
| EP | 2155287 A1 | 2/2010 |
| JP | 862-051630 B2 | 10/1987 |
| JP | 102-001275 A | 1/1990 |
| JP | H09-024026 A | 1/1997 |
| JP | 2008-051663 A | 3/2008 |
| JP | 2008-136673 A | 6/2008 |
| JP | 2010-172739 A | 8/2010 |
| JP | 2014-204779 A | 10/2014 |
| JP | 2015-112223 A | 6/2015 |
| JP | 2016-221028 A | 12/2016 |
| JP | 2017-106812 A | 6/2017 |
| JP | 2019-063439 A | 4/2019 |
| WO | 2007/040223 A1 | 4/2007 |
| WO | 2007/120812 A2 | 10/2007 |
| WO | 2008/106191 A2 | 9/2008 |
| WO | 2014/028103 A1 | 2/2014 |
| WO | 2014/093846 A1 | 6/2014 |
| WO | 2015/099932 A1 | 7/2015 |
| WO | 2017/015322 A1 | 1/2017 |
| WO | 2019221202 A1 | 11/2019 |
| WO | 2019221203 A1 | 11/2019 |
| WO | 2019221204 A1 | 11/2019 |
| WO | 2019221205 A1 | 11/2019 |

OTHER PUBLICATIONS

International Search Report dated Jun. 18, 2019 for Application No. PCT/JP2019/019394 published as WO2019221203.
Potentially related U.S. Appl. No. 15/823,794, filed Nov. 28, 2017 entitled "Medical Liquid-Pressure-Detecting Device", issued as U.S. Pat. No. 10,775,252 on Sep. 15, 2020.
Potentially related U.S. Appl. No. 17/093,817, filed Nov. 10, 2020 entitled "Pressure Detector," Published as WO2019221202.
Potentially related U.S. Appl. No. 17/093,823, filed Nov. 10, 2020 entitled "Pressure Detector," Published as WO2019221204.
Potentially related U.S. Appl. No. 17/093,825, filed Nov. 10, 2020 entitled "Pressure Detector," Published as WO2019221205.

* cited by examiner

[Fig. 1]
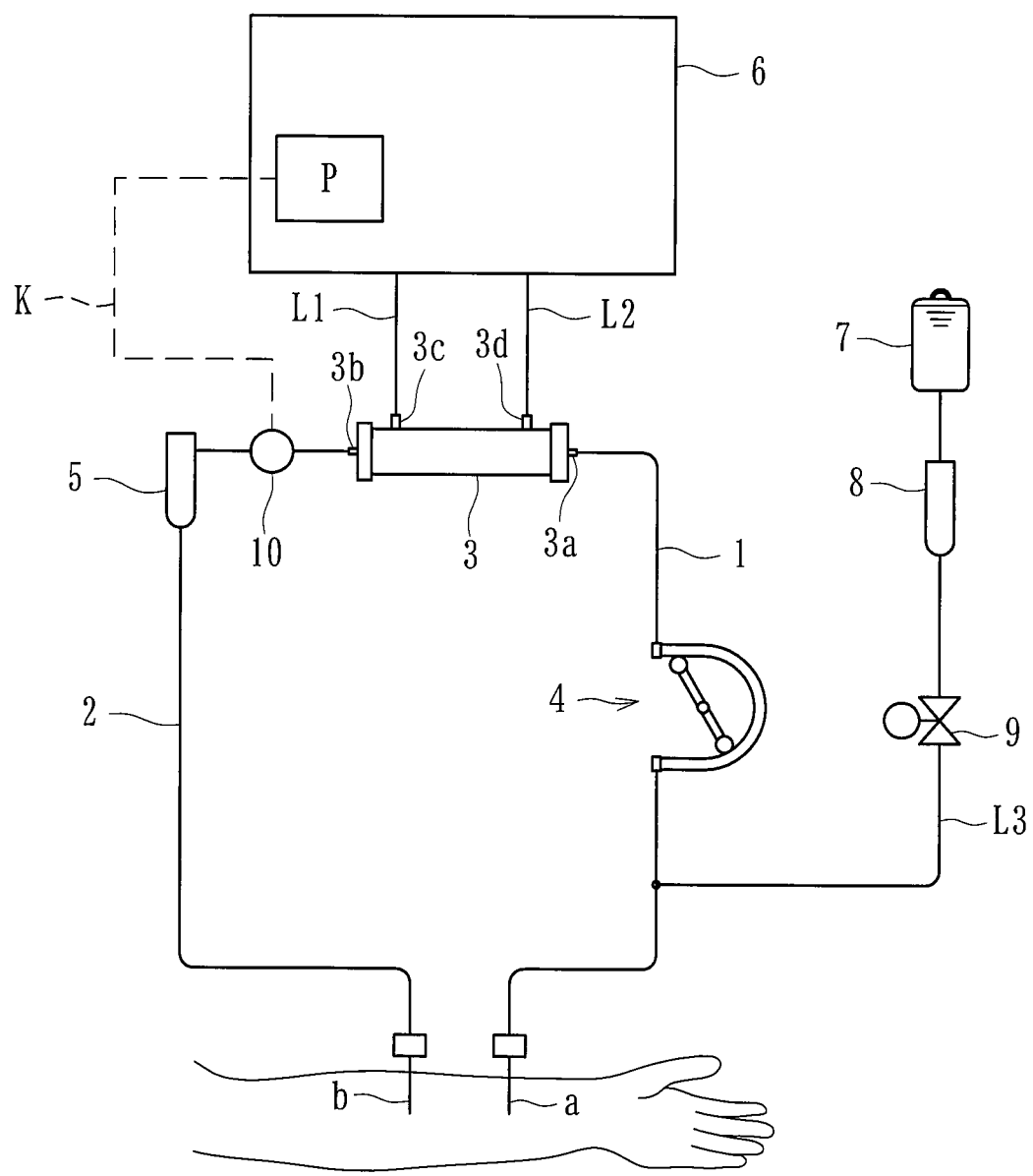

[Fig. 2]
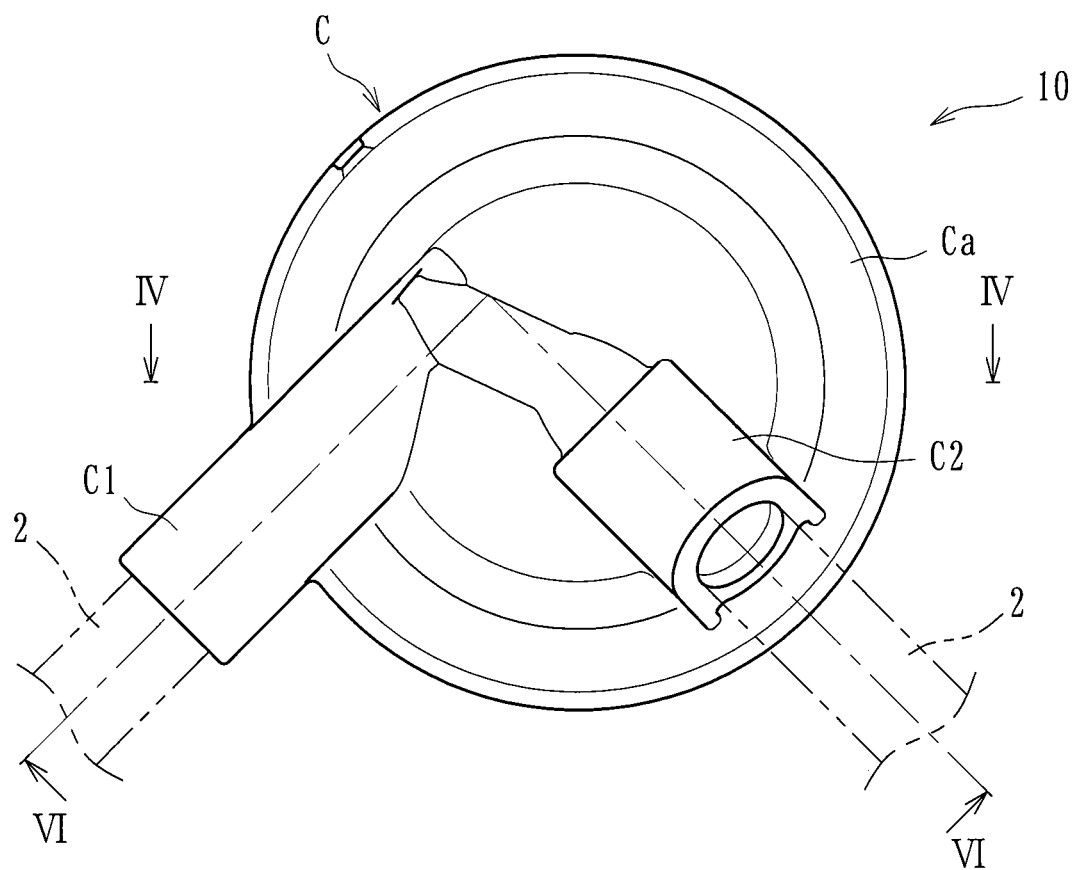

[Fig. 3]
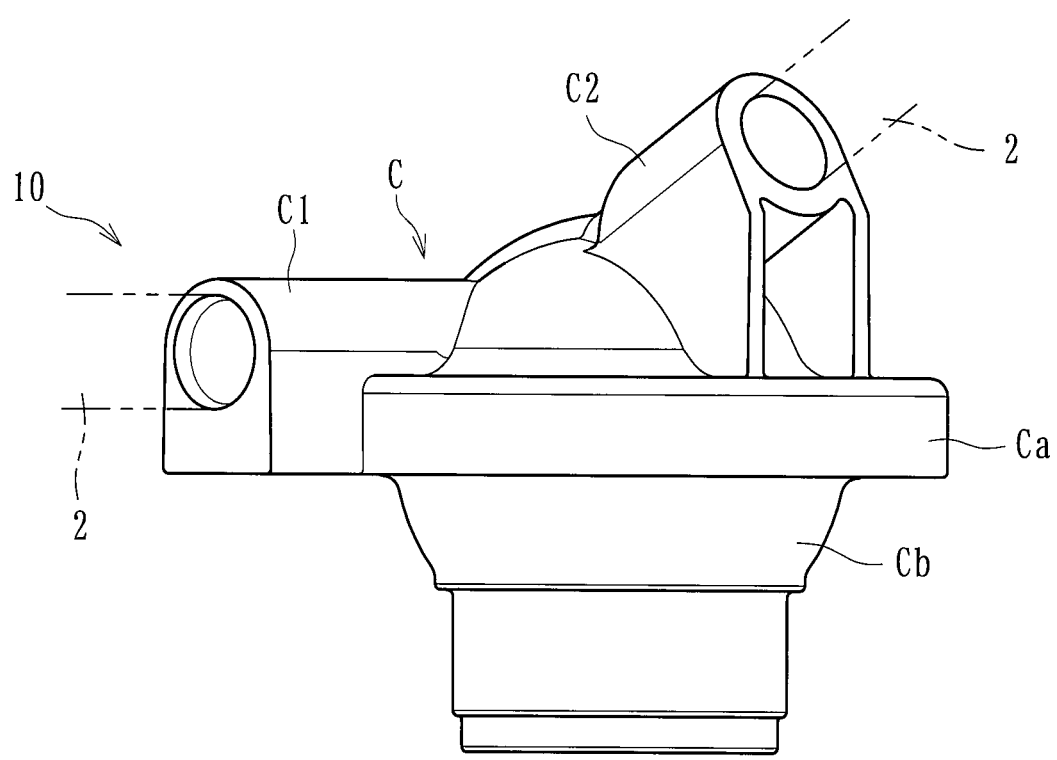

[Fig. 4]
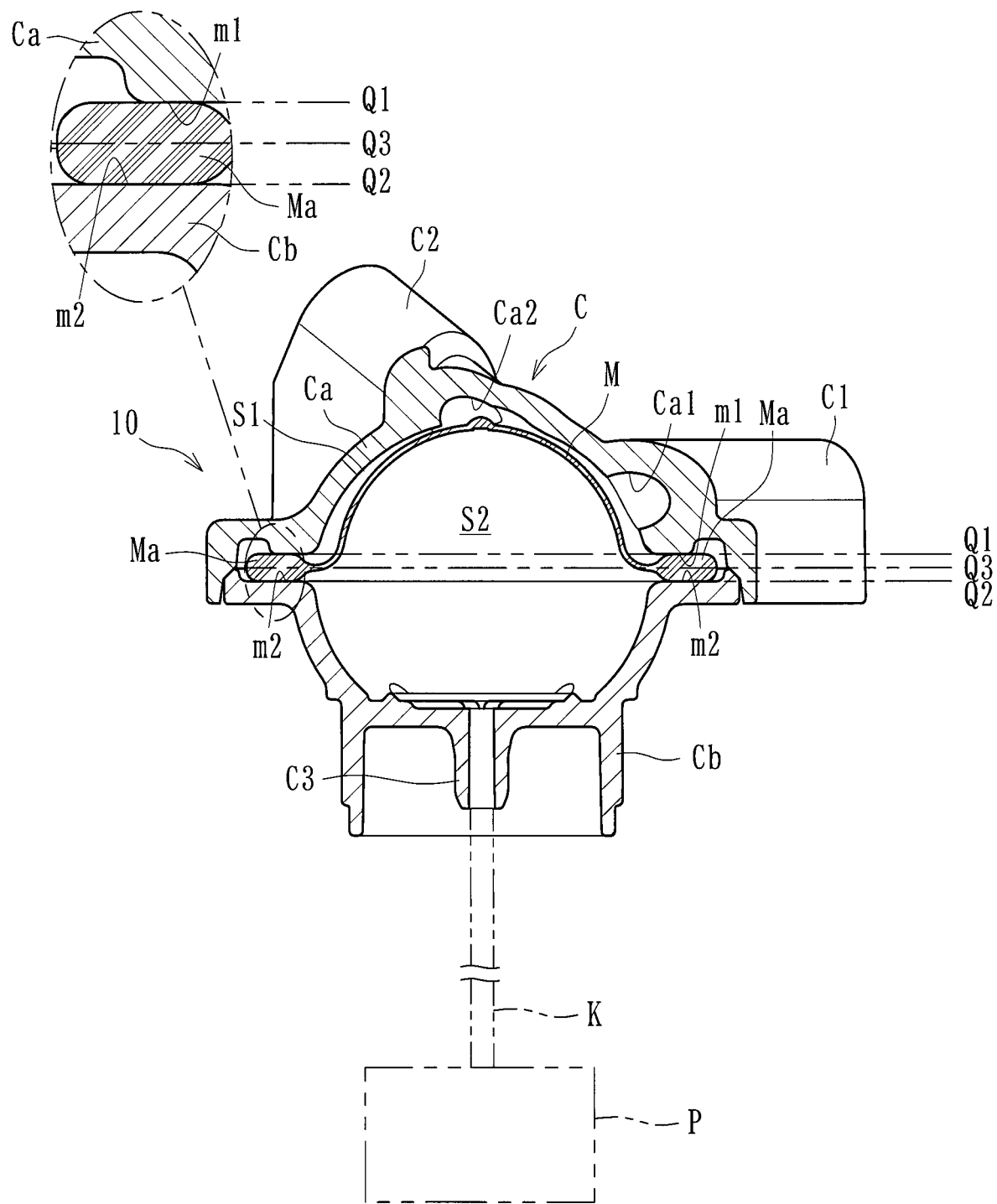

[Fig. 5]
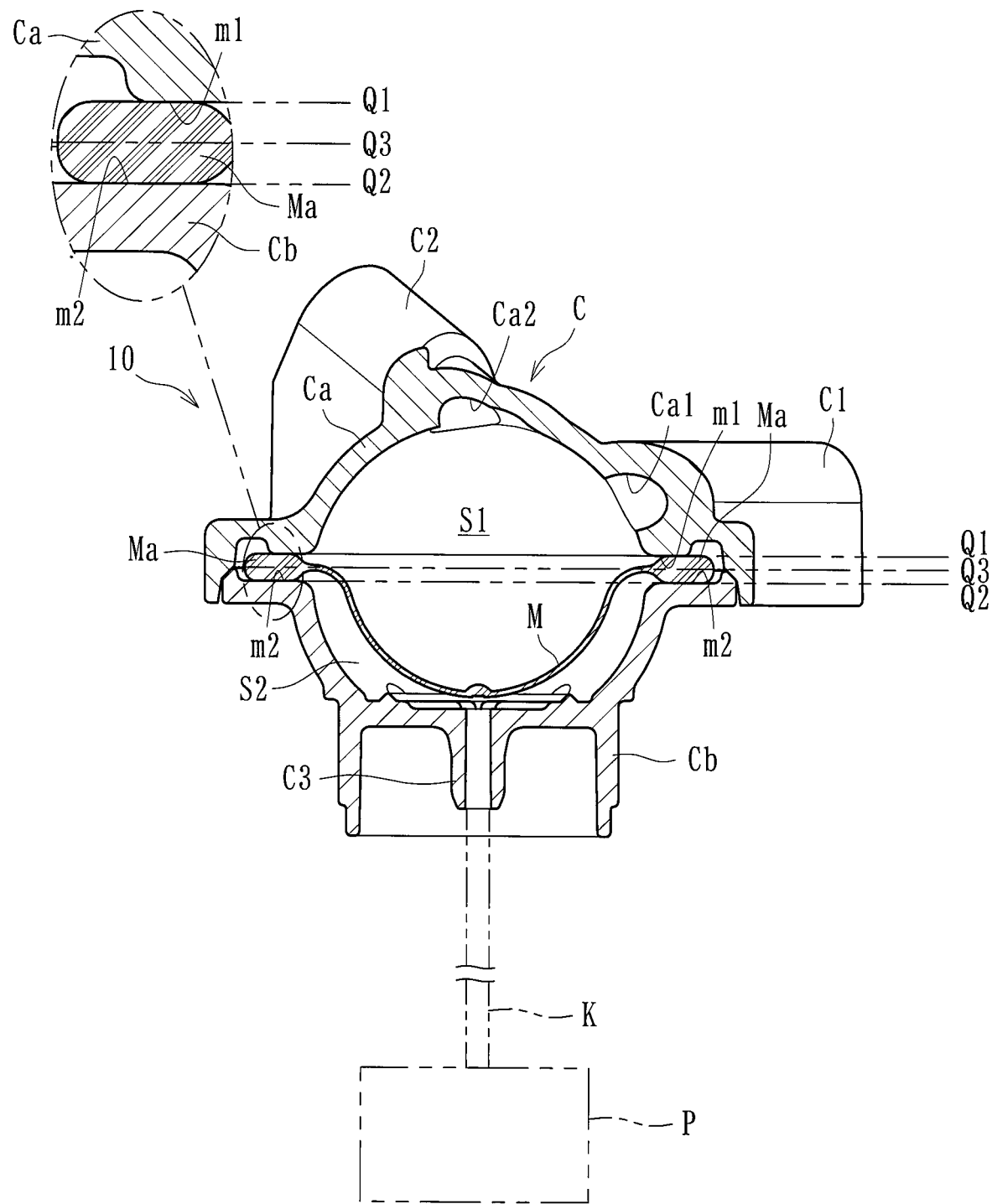

[ Fig. 6 ]
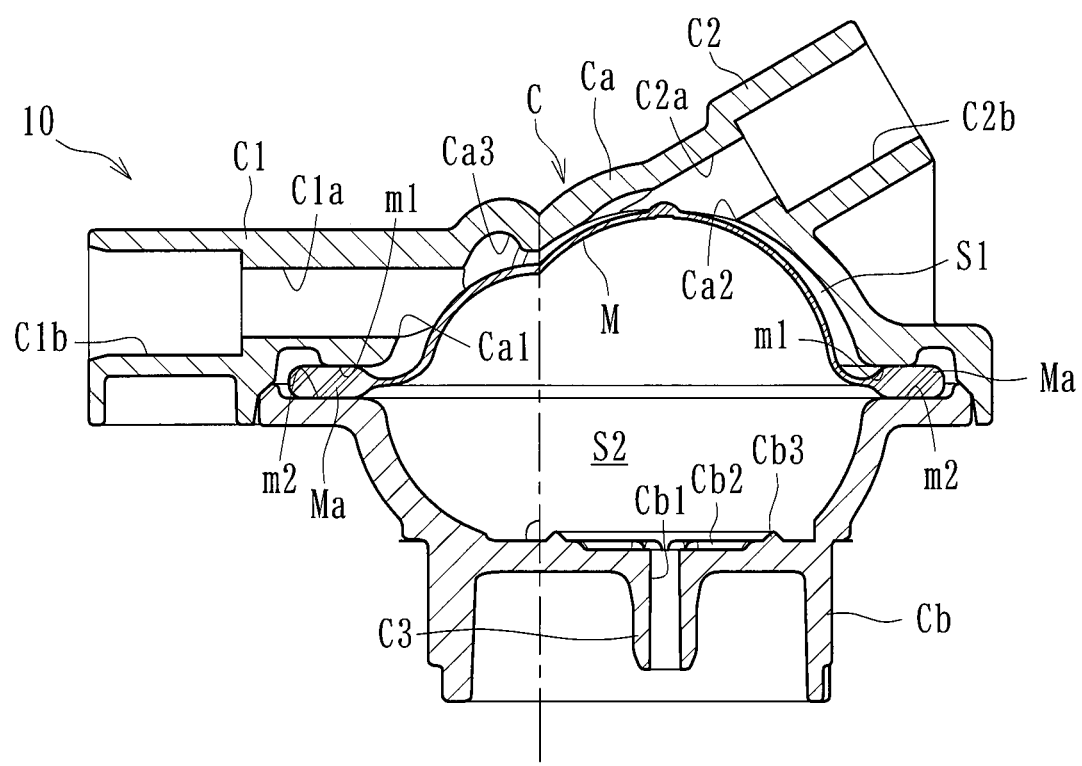

[Fig. 7]
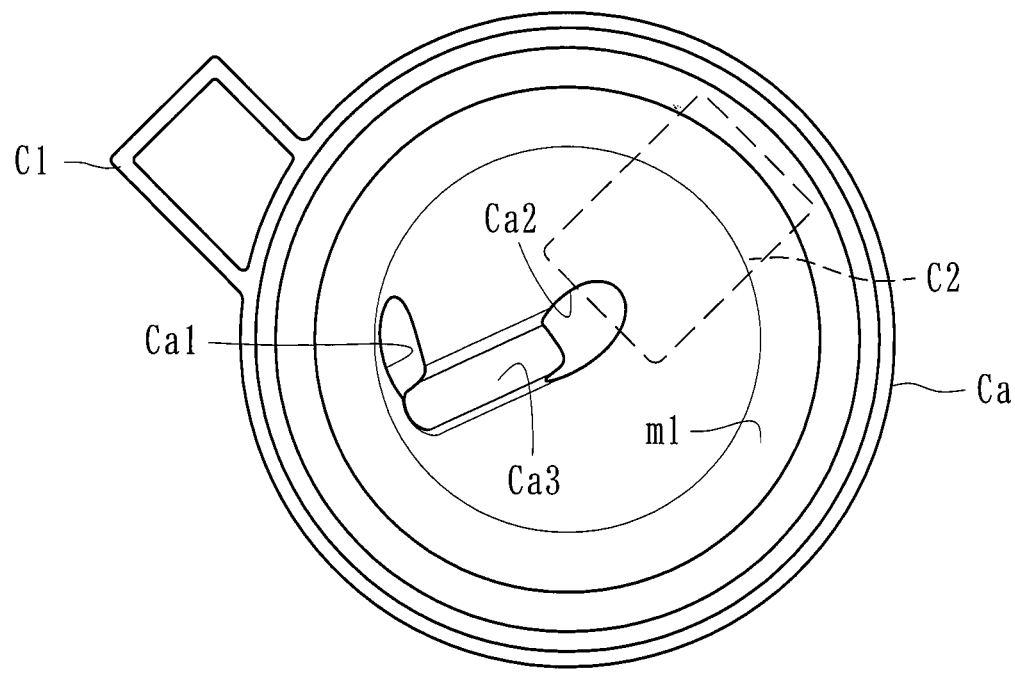
[Fig. 8]
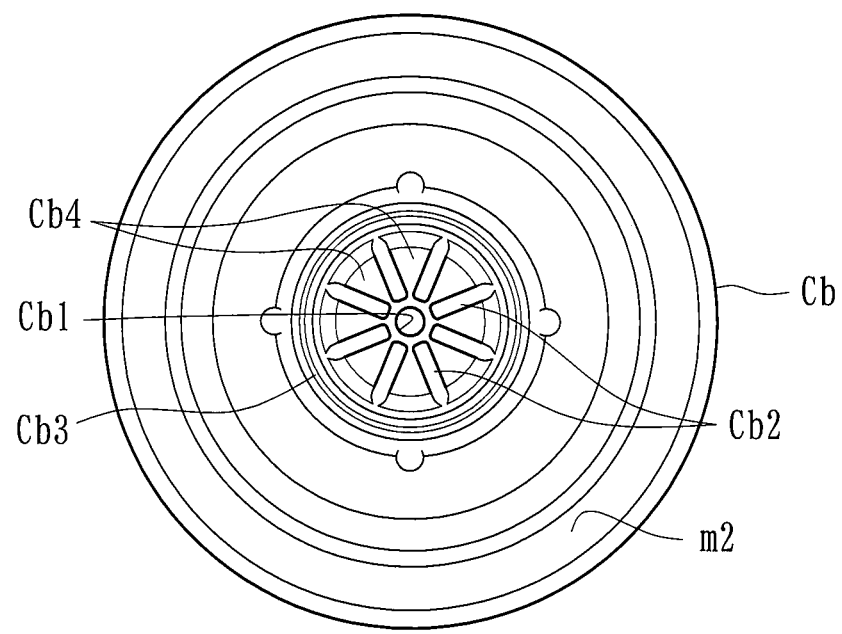

[Fig. 9]
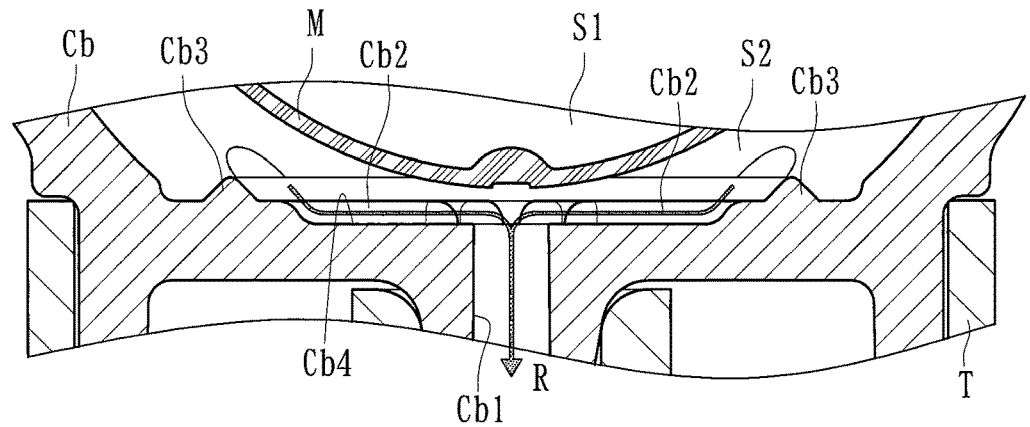
[Fig. 10]
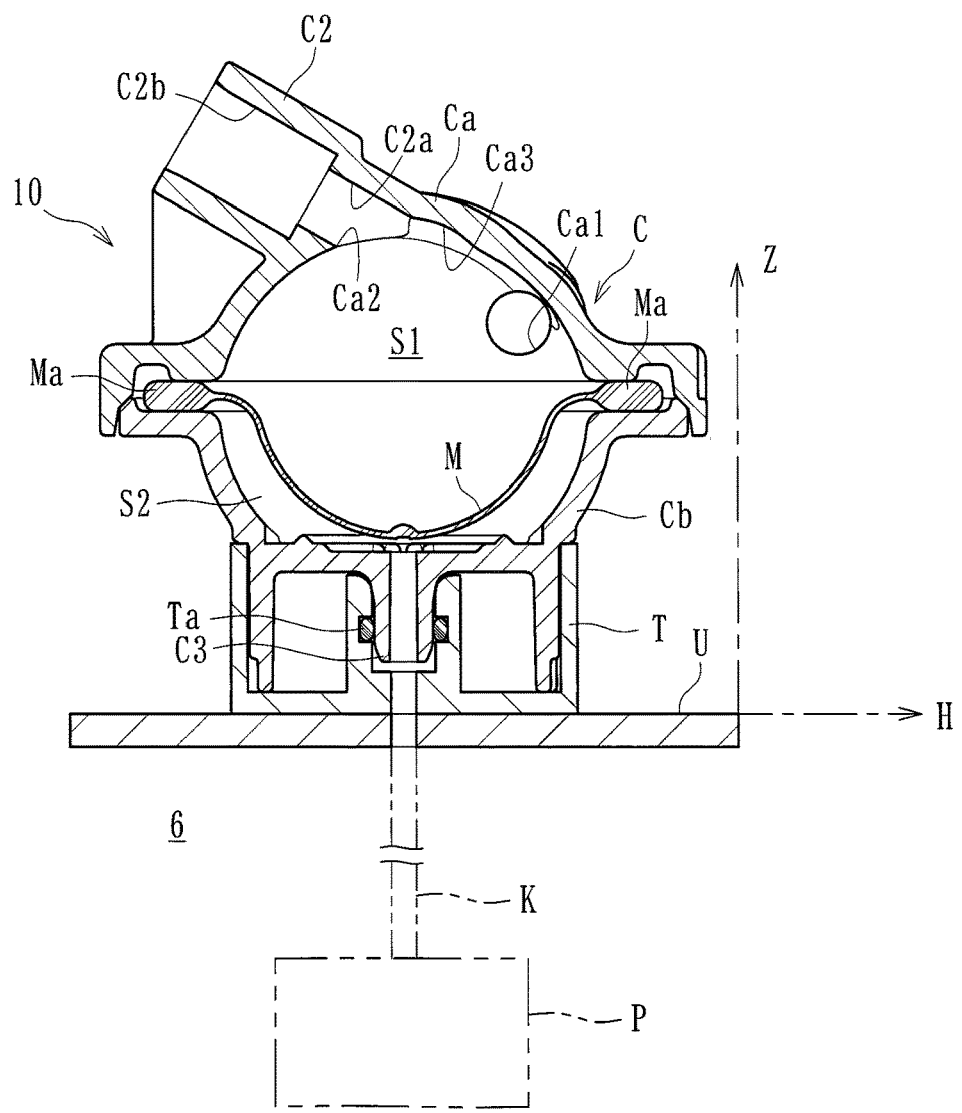

[ Fig. 11 ]
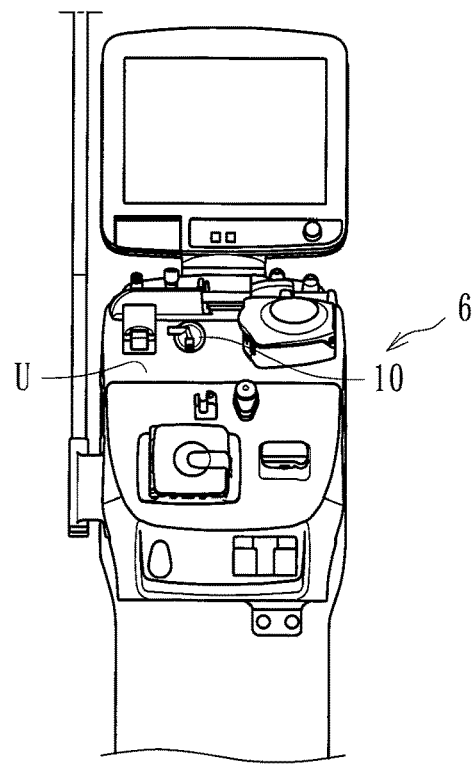
[ Fig. 12 ]
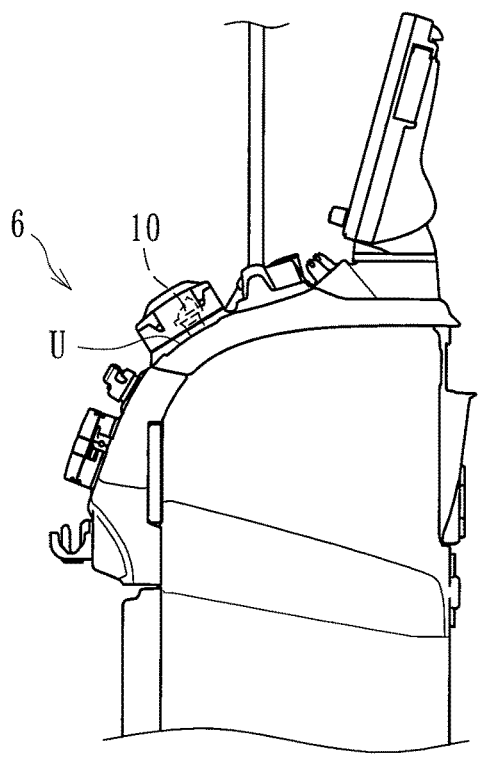

[ Fig. 13 ]
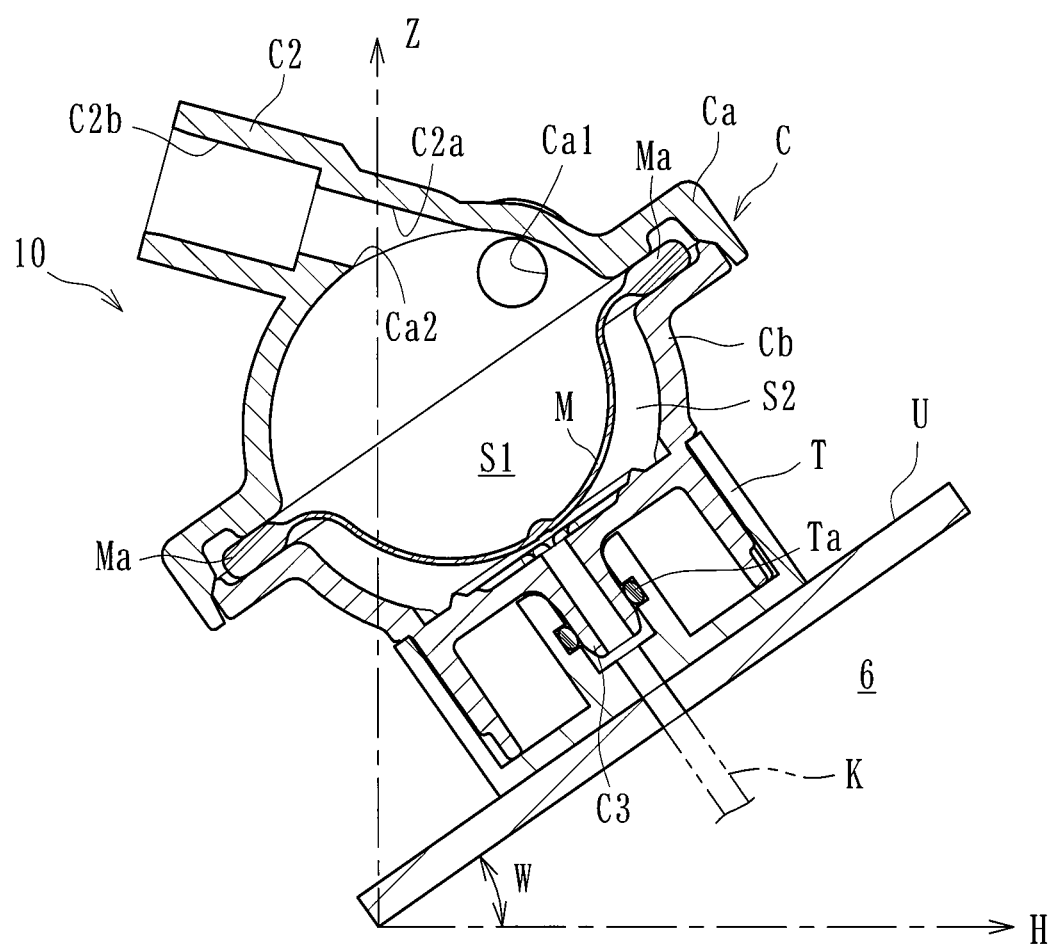

PRESSURE DETECTOR

CROSS-REFERENCE TO RELATED APPLICATION(S)

This application is a continuation of International Application No. PCT/JP2019/019394, filed on May 15, 2019, which claims priority to Japanese Application No. 2018-094463, filed on May 16, 2018, the entire disclosures of which are hereby incorporated by reference.

FIELD

The present invention relates to a pressure detector capable of detecting the pressure of liquid in a flow route by detecting the pressure in a gas-phase portion.

BACKGROUND

In general, dialysis treatment is performed by using a blood circuit for causing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and a venous puncture needle, respectively. The patient is punctured with the puncture needles, and extracorporeal circulation of blood in the dialysis treatment is thus performed.

To detect the pressure of blood that extracorporeally circulates through a blood circuit, a pressure detector has been proposed as disclosed by PTL 1, for example. The pressure detector includes a case connectable to a blood circuit, and a diaphragm (a membrane member) attached inside the case and with which a liquid-phase portion to be supplied with blood in the blood circuit and a gas-phase portion to be supplied with air are separated from each other, the diaphragm being displaceable in accordance with the pressure of the blood supplied to the liquid-phase portion, the pressure detector being capable of detecting the pressure of the blood by detecting the pressure in the gas-phase portion with a pressure detection sensor. With such a known pressure detector, since the liquid-phase portion and the gas-phase portion are separated from each other by the membrane member, the pressure of the blood in the blood circuit can be detected accurately while the blood is prevented from coming into contact with the air in the gas-phase portion.

In a state where the case of the above known pressure detector is attached to a predetermined attaching surface, if the liquid supplied to the liquid-phase portion contains some gas such as bubbles, the gas may be collected at the top (the highest part in the vertical direction) of the liquid-phase portion. Such a situation may adversely affect the detection of liquid pressure. To solve the above problem, the present applicant has proposed a pressure detector capable of discharging gas through an outlet opening provided at the top (the highest part in the vertical direction) of a liquid-phase portion thereof (see PTL 2).

PTL 1: Japanese Unexamined Patent Application Publication (Translation of PCT Application) No. 2017-504389 and PTL 2: Japanese Unexamined Patent Application Publication No. 2016-221028 the teachings of which are expressly incorporated by reference herein for all purposes.

SUMMARY

In the above known pressure detector including the liquid-phase portion having the outlet opening at the top, gas that has flowed into the liquid-phase portion can be discharged easily and assuredly. However, since an outlet port extends in a direction orthogonal to the vertical direction, it may be difficult to smoothly discharge liquid from the outlet opening. Moreover, such a configuration may cause a problem with the discharge of the gas.

The present teachings have been conceived in view of the above circumstances and provides a pressure detector in which the collection of gas in a liquid-phase portion in a state where a case thereof is attached to a predetermined attaching surface can be suppressed, and liquid and gas having flowed into the liquid-phase portion can be discharged therefrom smoothly through an outlet port.

Variation 1 may comprise a pressure detector that includes a case connectable to a flow route for liquid and attachable to a predetermined attaching surface; and a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion. The pressure detector includes an inlet port including a connecting portion connectable to the flow route for the liquid, and a flow-route portion through which the liquid flows into an inlet opening of the liquid-phase portion; and an outlet port including a connecting portion connectable to the flow route for the liquid, and a flow-route portion through which the liquid having flowed into the liquid-phase portion is discharged from an outlet opening. The outlet opening is positioned in a part of the liquid-phase portion that includes a highest point in a vertical direction in a state where the case is attached to the predetermined attaching surface, and the outlet port extends obliquely upward from the outlet opening.

Variation 2 may comprise the pressure detector according to variation 1, the predetermined attaching surface is a substantially horizontal surface inclined by 0 to 20 degrees with respect to a horizontal direction.

Variation 3 may comprise the pressure detector according to variation 1, the predetermined attaching surface is a surface inclined by 0 to 60 degrees with respect to a horizontal plane.

Variation 4 may comprise the pressure detector according to any of variations 1 to 3, the inlet port extends in a direction tangent to the liquid-phase portion in plan view in such a manner as to generate a vortex with the liquid flowing into the liquid-phase portion from the inlet opening.

Variation 5 may comprise the pressure detector according to any of variations 1 to 4, the case includes a liquid-phase-portion case defining the liquid-phase portion, and a gas-phase-portion case defining the gas-phase portion; the membrane member is held between the liquid-phase-portion case and the gas-phase-portion case that are mated to each other; and the inlet port extends substantially parallel to an attaching plane defined for the membrane member while the outlet port extends at a predetermined angle with respect to the attaching plane defined for the membrane member.

Variation 6 may comprise a blood circuit to which the pressure detector according to any of variations 1 to 5 is connected.

Variation 1 may comprise the outlet opening is positioned in the part of the liquid-phase portion that includes the highest point in the vertical direction in the state where the case is attached to the predetermined attaching surface. Furthermore, the outlet port extends obliquely upward from the outlet opening. Therefore, the collection of gas in the liquid-phase portion in the state where the case is attached to the predetermined attaching surface can be suppressed, and the liquid and gas having flowed into the liquid-phase portion can be discharged therefrom smoothly through the outlet port.

According to variation 2, the predetermined attaching surface is a substantially horizontal surface inclined by 0 to 20 degrees with respect to the horizontal direction. Therefore, the collection of gas in the liquid-phase portion in the state where the case is attached to the predetermined attaching surface can be suppressed assuredly, and the liquid and gas can be discharged more smoothly from the liquid-phase portion.

According to variation 3, the predetermined attaching surface is defined as a surface inclined by 0 to 60 degrees with respect to the horizontal plane. Therefore, even if the predetermined attaching surface is inclined, the collection of gas in the liquid-phase portion in the state where the case is attached to the predetermined attaching surface can be suppressed assuredly, and the liquid and gas can be discharged smoothly from the liquid-phase portion.

According to variation 4, the inlet port extends in the direction tangent to the liquid-phase portion in plan view in such a manner as to generate a vortex with the liquid flowing into the liquid-phase portion from the inlet opening. Therefore, the liquid in the liquid-phase portion can be stirred in a good manner. Thus, the retention of liquid and gas therein can be suppressed.

According to variation 5, the case includes the liquid-phase-portion case defining the liquid-phase portion, and the gas-phase-portion case defining the gas-phase portion. Furthermore, the membrane member is held between the liquid-phase-portion case and the gas-phase-portion case that are mated to each other. Furthermore, the inlet port extends substantially parallel to the attaching plane defined for the membrane member while the outlet port extends at the predetermined angle with respect to the attaching plane defined for the membrane member. Therefore, the liquid in the liquid-phase portion can be stirred in a better manner. Thus, the retention of liquid and gas therein can be suppressed more effectively.

According to variation 6, a blood circuit producing the advantageous effects of the pressure detector according to any of variations 1 to 5 can be provided.

BRIEF DESCRIPTION OF THE DRAWINGS

FIG. 1 is a schematic diagram illustrating a dialysis apparatus (a blood purification apparatus) to which a pressure detector according to an embodiment of the present invention is applied.

FIG. 2 is a plan view of the pressure detector.

FIG. 3 is a front view of the pressure detector.

FIG. 4 is a sectional view taken along line IV-IV illustrated in FIG. 2 (with a membrane member displaced toward the side of a liquid-phase portion).

FIG. 5 is a sectional view taken along line IV-IV illustrated in FIG. 2 (with the membrane member displaced toward the side of a gas-phase portion).

FIG. 6 is a sectional view taken along line VI-VI illustrated in FIG. 2.

FIG. 7 is a plan view of an inlet opening and an outlet opening provided in a liquid-phase-portion case included in the pressure detector.

FIG. 8 is a plan view of a gas-phase-portion case included in the pressure detector.

FIG. 9 is a sectional view of passages defined by ribs provided in the pressure detector.

FIG. 10 is a sectional view of the pressure detector with the case thereof attached to a predetermined attaching surface (a horizontal surface).

FIG. 11 is a front view of the dialysis device with the pressure detector attached to an attaching surface thereof.

FIG. 12 is a side view of the dialysis device with the pressure detector attached to the attaching surface thereof.

FIG. 13 is a sectional view of the pressure detector attached to the attaching surface of the dialysis device.

DETAILED DESCRIPTION

An embodiment of the present invention will now be described specifically with reference to the drawings.

A blood purification apparatus applied to the present embodiment is a dialysis apparatus for giving dialysis treatment and basically includes, as illustrated in FIG. 1, a blood circuit including an arterial blood circuit 1 and a venous blood circuit 2, a dialyzer 3 (a blood purifier) provided between the arterial blood circuit 1 and the venous blood circuit 2 and that purifies blood flowing through the blood circuit, a blood pump 4, an air-trap chamber 5 provided to the venous blood circuit 2, a dialysis device 6 that supplies dialysate to the dialyzer 3 and drains waste liquid from the dialyzer 3, a physiological-saline supply line L3 (a substitution-fluid supply line) that allows physiological saline as a substitution fluid to be supplied to the blood circuit, and a storage unit 7 that stores the physiological saline as the substitution fluid.

The arterial blood circuit 1 is provided with an arterial puncture needle (a) connectable to a distal end thereof through a connector, and the blood pump 4, which is of a peristaltic type, at a halfway position thereof. The venous blood circuit 2 is provided with a venous puncture needle (b) connectable to a distal end thereof through a connector, and the air-trap chamber 5 at a halfway position thereof. The air-trap chamber 5 is capable of trapping bubbles in the liquid and is provided with a filtering net (not illustrated), thereby being capable of trapping, for example, thrombi and the like at the time of blood return. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The blood pump 4, which is a peristaltic pump provided to the arterial blood circuit 1, is capable of undergoing normal rotation and reverse rotation and causing the liquid in the blood circuit to flow in the direction of rotation thereof. Specifically, the arterial blood circuit 1 includes a squeezable tube that is softer and has a larger diameter than other flexible tubes forming the arterial blood circuit 1. The blood pump 4 includes rollers for squeezing the squeezable tube in the direction of liquid delivery. When the blood pump 4 is activated, the rollers rotate and thus squeeze the squeezable tube (a portion of the blood circuit), whereby the liquid in the tube can be made to flow in the direction of rotation (the direction in which the rollers rotate).

When the blood pump 4 is activated to undergo normal rotation (leftward rotation in the drawing) while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patient's body. That is, the patient's blood is purified with the dialyzer 3 while being caused to extracorporeally circulate through the blood circuit from the distal end of the arterial blood circuit 1 to the distal end of the venous blood circuit 2. When the blood pump 4 is activated to undergo reverse rotation (rightward rotation in the drawing), the blood in the blood circuit (a portion of the arterial blood circuit 1 that is between the distal end and a position where the blood pump 4 is provided) can be returned to the patient.

The dialyzer 3 has, in a housing thereof, a blood introduction port 3a, a blood delivery port 3b, a dialysate introduction port 3c, and a dialysate delivery port 3d. The blood introduction port 3a is connected to the arterial blood circuit 1. The blood delivery port 3b is connected to the venous blood circuit 2. The dialysate introduction port 3c and the dialysate delivery port 3d are connected to a dialysate introduction line L1 and a dialysate drain line L2, respectively, extending from the dialysis device 6.

The dialyzer 3 houses a plurality of hollow fibers. Spaces inside the respective hollow fibers form flow routes for blood, and spaces between the inner surface of the housing and the outer surfaces of the hollow fibers form flow routes for dialysate. The hollow fibers each have a number of microscopic holes (pores) extending therethrough from the outer surface to the inner surface, thereby forming a hollow fiber membrane. Impurities and the like contained in the blood are allowed to permeate through the hollow fiber membranes into the dialysate.

On the other hand, the dialysis device 6 includes a liquid delivery unit such as a duplex pump provided over the dialysate introduction line L1 and the dialysate drain line L2. A bypass line that bypasses the liquid delivery unit is provided with an ultrafiltration pump for removing water from the patient's blood flowing in the dialyzer 3. One end of the dialysate introduction line L1 is connected to the dialyzer 3 (the dialysate introduction port 3c), and the other end is connected to a dialysate supply device (not illustrated) that prepares a dialysate at a predetermined concentration. One end of the dialysate drain line L2 is connected to the dialyzer 3 (the dialysate delivery port 3d), and the other end is connected to a drainage unit, not illustrated. The dialysate supplied from the dialysate supply device flows through the dialysate introduction line L1 into the dialyzer 3, and further flows through the dialysate drain line L2 into the drainage unit.

The air-trap chamber 5 is provided with an overflow line extending from the top thereof. The overflow line is provided with a clamp unit, such as an electromagnetic valve, at a halfway position thereof. When the clamp unit such as an electromagnetic valve is opened, the liquid (a priming solution or the like) flowing in the blood circuit can be made to overflow through the overflow line.

The physiological-saline supply line L3 (the substitution-fluid supply line) is connected at one end thereof to the arterial blood circuit 1 between the position where the blood pump 4 is provided and the distal end of the arterial blood circuit 1 through a T-shaped pipe or the like. The physiological-saline supply line L3 forms a flow route (such as a flexible tube or the like) through which the physiological saline (the substitution fluid) to substitute for the blood in the blood circuit is allowed to be supplied to the arterial blood circuit 1. The physiological-saline supply line L3 is provided at the other end thereof with the storage unit 7 (a so-called "saline bag"), in which a predetermined amount of physiological saline is stored. The physiological-saline supply line L3 is further provided at a halfway position thereof with an air-trap chamber 8.

The physiological-saline supply line L3 according to the present embodiment is further provided with a clamp unit 9 (such as an electromagnetic valve or the like). The clamp unit 9 is capable of opening and closing the physiological-saline supply line L3, thereby closing and opening the flow route. The state of the physiological-saline supply line L3 is arbitrarily switchable by opening or closing the clamp unit 9, between a closed state where the flow route is closed and an open state where the physiological saline (substitution fluid) is allowed to flow. The clamp unit 9 may be replaced with a general-purpose device such as a pair of forceps with which the flow route of the physiological-saline supply line L3 can be manually closed and opened.

The blood circuit applied to the present embodiment is provided with a pressure detector 10. The pressure detector 10 is connected to the venous blood circuit 2 at a position between the dialyzer 3 and the air-trap chamber 5 and is capable of detecting the pressure of the blood flowing in the venous blood circuit 2 (the blood circuit). Specifically, as illustrated in FIGS. 2 to 6, the pressure detector 10 includes a case C connectable to the flow route for liquid (in the present embodiment, the venous blood circuit 2 (the blood circuit)), and a membrane member M attached inside the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P.

The case C is a hollow molded component obtained by molding a predetermined resin material or the like. The case C is a combination of a liquid-phase-portion case Ca defining the liquid-phase portion S1 and a gas-phase-portion case Cb defining the gas-phase portion S2. The liquid-phase-portion case Ca has an inlet port C1 and an outlet port C2 integrally molded therewith. The inlet port C1 and the outlet port C2 are each connectable to the flow route for liquid and allow the flow route to communicate with the liquid-phase portion S1. The gas-phase-portion case Cb has a connection port C3 integrally molded therewith. The connection port C3 is connectable to one end of the pipe K, to be described below, and allows the one end to communicate with the gas-phase portion S2.

The liquid-phase-portion case Ca has an annular holding surface m1 (see FIG. 7) at the periphery thereof. The gas-phase-portion case Cb has an annular holding surface m2 (see FIG. 8) at the periphery thereof. When the liquid-phase-portion case Ca and the gas-phase-portion case Cb are mated to each other, a rim Ma of the membrane member M is placed between the holding surface m1 and the holding surface m2. Thus, the membrane member M can be attached in a sealing manner. A space thus provided in the case C is separated (sectioned) by the membrane member M into the liquid-phase portion S1 and the gas-phase portion S2.

The membrane member M serves as a diaphragm attached inside the case C and is made of a flexible material that is displaceable or deformable in conformity with pressure change occurring in the liquid-phase portion S1 or the gas-phase portion S2. Specifically, if the pressure of the liquid (the hydraulic pressure) in the liquid-phase portion S1 is low, as illustrated in FIG. 4, the membrane member M is displaced toward the side of the liquid-phase portion S1, whereby the capacity of the gas-phase portion S2 is increased. If the pressure of the liquid (the hydraulic pressure) in the liquid-phase portion S1 is high, as illustrated in FIG. 5, the membrane member M is displaced toward the side of the gas-phase portion S2, whereby the capacity of the gas-phase portion S2 is reduced.

The gas-phase-portion case Cb has an opening Cb1 (see FIG. 8) substantially at the center of the bottom thereof. The opening Cb1 provided in the inner surface (the bottom) of the gas-phase-portion case Cb allows the flow route in the connection port C3 and the gas-phase portion S2 to communicate with each other. Accordingly, air (gas) is allowed to be introduced into or discharged from the gas-phase portion S2 in accordance with the displacement of the membrane member M. The pipe K is connected at one end thereof to the connection port C3 and at the other end thereof to the pressure detection sensor P. Therefore, as air (gas) is introduced or discharged through the opening Cb1 with the displacement of the membrane member M, the pressure detection sensor P can detect the pressure in the gas-phase portion S2. Note that the connection port C3 is not limited to the one to be connected to the pipe K and may be connected to another element capable of transmitting the pressure in the gas-phase portion S2 to the pressure detection sensor P.

The gas-phase-portion case Cb according to the present embodiment has recesses Cb4 surrounding the opening Cb1 provided at the bottom thereof, and an annular ridge Cb3 provided at the periphery thereof on the outer side with respect to the recesses Cb4. Furthermore, as illustrated in FIG. 8, the gas-phase portion S2 has a plurality of ribs Cb2 in the recesses Cb4 and around the opening Cb1. The ribs Cb2 project radially about the opening Cb1 and thus define passages R.

The passages R according to the present embodiment are secured for the introduction or discharge of the gas through the opening Cb1 during the displacement of the membrane member M toward the side of the gas-phase portion S2. As illustrated in FIG. 9, in a state where the membrane member M displaced toward the side of the gas-phase portion S2 is in contact with the ribs Cb2, the passages R are provided as spaces (spaces in the recesses Cb4) provided around the opening Cb1 and being continuous with the opening Cb1. That is, during the displacement of the membrane member M toward the side of the gas-phase portion S2, gaps between the ribs Cb2 serve as the passages R, through which the gas (air in the gas-phase portion S2) is allowed to flow. Thus, the introduction or discharge of the gas through the opening Cb1 is ensured. Note that the ribs Cb2 for providing the passages R may be replaced with grooves provided around the opening Cb1 of the gas-phase portion S2.

Furthermore, a hydrophobic membrane may be provided over the recesses Cb4 inclusive of the opening Cb1. In that case, it is preferable that the hydrophobic membrane be a member formed as a membrane that allows gas to pass therethrough but blocks liquid from passing therethrough, and that the periphery of the hydrophobic membrane be welded (for example, by ultrasonic welding or the like) to the ridge Cb3 provided around the opening Cb1.

The inlet port C1 according to the present embodiment is a portion (a projected portion) connectable to the flow route for liquid (the blood circuit) and includes, as illustrated in FIGS. 4 and 6, a flow-route portion C1a through which the liquid (blood) flows into an inlet opening Ca1 (see FIG. 7) of the liquid-phase portion S1, and a connecting portion C1b connectable to the flow route (the blood circuit). Specifically, the flow-route portion C1a and the connecting portion C1b are continuous with each other in the axial direction thereof in the projected portion forming the inlet port C1. When a tube forming the flow route is connected to the connecting portion C1b, the liquid in the flow route can be made to flow into the flow-route portion C1a and then into the liquid-phase portion S1 through the inlet opening Ca1. Note that the inlet port C1 may be shaped as a recess to which the tube forming the flow route is to be connected.

The outlet port C2 according to the present embodiment is a portion (a projected portion) connectable to the flow route for liquid (the blood circuit) and includes, as illustrated in the drawings, a flow-route portion C2a through which the liquid (blood) having flowed into the liquid-phase portion S1 is discharged from an outlet opening Ca2 (see FIG. 7), and a connecting portion C2b connectable to the flow route (the blood circuit). Specifically, the flow-route portion C2a and the connecting portion C2b are continuous with each other in the axial direction thereof in the projected portion forming the outlet port C2. When a tube forming the flow route is connected to the connecting portion C2b, the liquid having flowed into the liquid-phase portion S1 can be made to flow into the flow-route portion C2a and then to be discharged to a flow route (the blood circuit) on the downstream side. Note that the outlet port C2 may be shaped as a recess to which the tube forming the flow route is to be connected.

The case C is attached to a predetermined attaching surface U defined on the dialysis device 6. As illustrated in FIG. 10, the attaching surface U according to the present embodiment is a substantially horizontal surface inclined by 0 to 20 degrees with respect to a horizontal direction H. The pressure detector 10 is fitted into an attaching member T provided on the attaching surface U, whereby the connection port C3 is connected to the pipe K. Thus, the pressure detector 10 is attached. Note that reference sign Ta in the drawing refers to a seal member, such as an O ring, which can seal the connection port C3 by coming into contact therewith.

As illustrated in the drawing, the outlet opening Ca2 according to the present embodiment is positioned in a part of the liquid-phase portion S1 that includes the highest point (the top in the attached state) in a vertical direction Z in a state where the case C is attached to the predetermined attaching surface U. Furthermore, the outlet port C2 extends (projects) obliquely upward from the outlet opening Ca2. Specifically, since the outlet opening Ca2 is positioned in the part including the highest point (the top) in the vertical direction Z in the state where the case C is attached to the predetermined attaching surface U, gas such as air in the liquid-phase portion S1 flows upward with its buoyancy and reaches the outlet opening Ca2. Then, the gas smoothly flows with its buoyancy through the outlet port C2 extending obliquely upward and is discharged to the outside.

The outlet opening Ca2 according to the present embodiment is positioned in the part of the liquid-phase portion S1 that includes the highest point (the top in the attached state) in the vertical direction Z in the state where the case C is attached to the predetermined attaching surface U. Therefore, the position of the outlet opening Ca2 is higher than the position of the inlet opening Ca1. Accordingly, the liquid (blood) and gas (bubbles) having flowed into the liquid-phase portion S1 from the inlet opening Ca1 flow toward the outlet opening Ca2 positioned thereabove.

The inlet port C1 according to the present embodiment extends (projects) in a direction tangent to the liquid-phase portion S1 in plan view (see FIG. 2) in such a manner as to generate a vortex with the liquid flowing into the liquid-phase portion S1 from the inlet opening Ca1. As described above, the case C according to the present embodiment includes the liquid-phase-portion case Ca defining the liquid-phase portion S1, and the gas-phase-portion case Cb defining the gas-phase portion S2. Furthermore, the membrane member M is held between the liquid-phase-portion case Ca and the gas-phase-portion case Cb that are mated to each other. Furthermore, the inlet port C1 extends (projects) substantially parallel to an attaching plane Q defined for the membrane member M while the outlet port C2 extends (projects) at a predetermined angle with respect to the attaching plane Q defined for the membrane member M.

The attaching plane Q defined for the membrane member M is the reference for defining the direction in which the inlet port C1 and the outlet port C2 are made to extend (project). As illustrated in FIGS. 4 and 5, the attaching plane Q, which is a virtual plane Q1 containing the holding surface m1 of the liquid-phase-portion case Ca, may be a virtual plane Q2 containing the holding surface m2 of the gas-phase-portion case Cb, or a virtual plane Q3 containing a plane extending along the height-direction center of the rim Ma of the membrane member M. That is, in the present invention, the attaching plane Q is any of the attaching plane Q1 containing the holding surface m1 of the liquid-phase-portion case Ca, the attaching plane Q2 containing the holding surface m2 of the gas-phase-portion case Cb, and the attaching plane Q3 containing the plane extending along the height-direction center of the rim Ma of the membrane member M. Furthermore, the inlet port C1 extends (projects) substantially parallel to the attaching plane Q while the outlet port C2 extends (projects) at a predetermined angle (obliquely upward) with respect to the attaching plane Q. The inclination of the outlet port C2 according to the present embodiment is about 30 degrees. In view of good handleability of the blood circuit, the inclination is preferably about 10 to 50 degrees.

The embodiment where the present pressure detector 10 is attached to the attaching surface U defined on the dialysis device 6 will further be described.

As described above, the dialysis device 6 is provided with medical components, such as the duplex pump and the ultrafiltration pump, necessary for the treatment. As illustrated in FIGS. 11 and 12, the dialysis device 6 has, on the front face thereof, the attaching surface U to which the case C is to be attached. As illustrated in FIG. 13, the attaching surface U is inclined by a predetermined angle W with respect to the horizontal direction H and is provided with the attaching member T at a predetermined position.

The inclination angle W of the attaching surface U only needs to be 0 to 60 degrees. In the present embodiment, the inclination angle W is about 35 degrees. As described above, the attaching surface U defined on the dialysis device 6 may be a substantially horizontal surface inclined by 0 to 20 degrees with respect to the horizontal direction H. The connection port C3 is connected to the seal member Ta of the attaching member T, whereby the case C is attached to the attaching surface U. In such an attached state, the outlet opening Ca2 is positioned in a part of the liquid-phase portion S1 that includes the highest point (the top in the attached state) in the vertical direction Z, and the outlet port C2 extends (projects) obliquely upward from the outlet opening Ca2.

According to the present embodiment, the outlet opening Ca2 is positioned in the part (a top position) of the liquid-phase portion S1 that includes the highest point in the vertical direction Z in the state where the case C is attached to the predetermined attaching surface U. Furthermore, the outlet port C2 extends (projects) obliquely upward from the outlet opening Ca2. Therefore, the collection of gas in the liquid-phase portion S1 in the state where the case C is attached to the predetermined attaching surface U can be suppressed, and the liquid and gas having flowed into the liquid-phase portion S1 can be discharged therefrom smoothly through the outlet port C2.

Furthermore, if the predetermined attaching surface U is a substantially horizontal surface inclined by 0 to 20 degrees with respect to the horizontal direction H, the collection of gas in the liquid-phase portion S1 in the state where the case C is attached to the predetermined attaching surface U can be suppressed assuredly, and the liquid and gas can be discharged more smoothly from the liquid-phase portion S1. Furthermore, the predetermined attaching surface may be defined as a surface inclined by 0 to 60 degrees with respect to the horizontal plane. Therefore, even if the predetermined attaching surface U is inclined, the collection of gas in the liquid-phase portion S1 in the state where the case C is attached to the predetermined attaching surface U can be suppressed assuredly, and the liquid and gas can be discharged smoothly from the liquid-phase portion S1.

Furthermore, the inlet port C1 according to the present embodiment extends (projects) in the direction tangent to the liquid-phase portion S1 in plan view in such a manner as to generate a vortex with the liquid flowing into the liquid-phase portion S1 from the inlet opening Ca1. Therefore, the liquid in the liquid-phase portion S1 can be stirred in a good manner. Thus, the retention of liquid and gas therein can be suppressed. Note that the inlet port C1 may be provided at another position or extend (project) in another direction, as long as the outlet opening Ca2 is positioned in a part of the liquid-phase portion S1 that includes the highest point in the vertical direction in the state where the case C is attached to the predetermined attaching surface U, and the outlet port C2 extends (projects) obliquely upward from the outlet opening Ca2.

Furthermore, the case C according to the present embodiment includes the liquid-phase-portion case Ca defining the liquid-phase portion S1, and the gas-phase-portion case Cb defining the gas-phase portion S2. Furthermore, the membrane member M is held between the liquid-phase-portion case Ca and the gas-phase-portion case Cb that are mated to each other. Furthermore, the inlet port C1 extends (projects) substantially parallel to the attaching plane Q defined for the membrane member M while the outlet port C2 extends (projects) at a predetermined angle with respect to the attaching plane Q defined for the membrane member M. Therefore, the liquid in the liquid-phase portion S1 can be stirred in a better manner. Thus, the retention of liquid and gas therein can be suppressed more effectively. Furthermore, according to the present embodiment, a blood circuit producing the above advantageous effects of the pressure detector 10 can be provided.

While the embodiment has been described above, the present invention is not limited thereto. The pressure detector 10 may be connected to another position of the blood circuit (for example, a position of the arterial blood circuit 1 between the distal end and the blood pump 4, or a position of the arterial blood circuit 1 between the blood pump 4 and the dialyzer 3). The blood circuit to which the present pressure detector 10 is to be connected may be of another type. For example, the blood circuit may be provided with not the air-trap chamber 5 but the present pressure detector 10 instead.

Furthermore, while the above embodiment concern a case where the plurality of ribs Cb2 are arranged radially about the opening Cb1, the ribs Cb2 may be omitted, or another irregular pattern may be provided. While the above embodiment concerns a case where the pressure detector is attachable to the attaching surface U defined on the dialysis device 6, the attaching surface U may be defined at a position other than the dialysis device 6.

While the above embodiment concerns the pressure detector 10 provided to the blood circuit intended for dialysis treatment, the present invention may be applied to a pressure detector provided to another blood circuit to be used in a treatment of purifying blood of a patient. For example, the present invention may be applied to a pressure detector provided to a blood circuit to be used in acetate-free biofiltration (AFBF), continuous slow hemofiltration, hemoadsorption, selective cytapheresis, plasma exchange, double filtration plasmapheresis, plasma adsorption, or the like.

The present invention is applicable to any pressure detector of any other type or for any other use, as long as an outlet opening is positioned in a part of a liquid-phase portion that includes the highest point in the vertical direction in a state where a case is attached to a predetermined attaching surface, and an outlet port extends obliquely upward from the outlet opening.

REFERENCE SIGN LIST 1 arterial blood circuit
2 venous blood circuit
3 dialyzer (blood purifier)
4 blood pump
5 air-trap chamber
6 dialysis device
7 storage unit
8 air-trap chamber
9 clamp unit
10 pressure detector
L1 dialysate introduction line
L2 dialysate drain line
L3 physiological-saline supply line
C case
Ca liquid-phase-portion case
Ca1 inlet opening
Ca2 outlet opening
Cb gas-phase-portion case
Cb1 opening
C1 inlet port
C1a flow-route portion
C1b connecting portion
C2 outlet port
C2a flow-route portion
C2b connecting portion
C3 connection port
M membrane member
P pressure detection sensor
S1 liquid-phase portion
S2 gas-phase portion
K pipe
B hydrophobic membrane Q (Q1, Q2, Q3) attaching plane (defined for membrane member)
U attaching surface (defined for case)

The invention claimed is:

1. A pressure detector comprising:
a case connectable to a flow route for liquid and attachable to a predetermined attaching surface, the case comprising:
a liquid-phase-portion case defining a liquid-phase portion and
a gas-phase-portion case defining a gas-phase portion; and
a membrane member attached inside and between the liquid-phase-portion case and the gas-phase-portion case when the liquid-phase-portion case and the gas-phase-portion case are mated together so that the liquid-phase portion to be supplied with the liquid in the flow route and the gas-phase portion to be supplied with gas are separated from each other by the membrane member, the membrane member being displaceable in accordance with a pressure of the liquid supplied to the liquid-phase portion,
the pressure detector detecting the pressure of the liquid in the flow route by detecting a pressure in the gas-phase portion, the pressure detector comprising:
an inlet port including a connecting portion connectable to the flow route for the liquid, and a flow-route portion through which the liquid flows into an inlet opening of the liquid-phase portion, wherein the inlet port extends substantially parallel to an attaching plane defined for the membrane member; and
an outlet port including a connecting portion connectable to the flow route for the liquid, and a flow-route portion through which the liquid having flowed into the liquid-phase portion is discharged from an outlet opening, wherein the outlet port extends at a predetermined angle with respect to the attaching plane defined for the membrane member,
wherein the outlet opening is positioned in a part of the liquid-phase portion that includes a highest point in a vertical direction in a state where the case is attached to the predetermined attaching surface, and the outlet port extends obliquely upward from the outlet opening.

2. The pressure detector according to claim 1, wherein the predetermined attaching surface is a substantially horizontal surface inclined by 0 to 20 degrees with respect to a horizontal direction.

3. The pressure detector according to claim 1, wherein the predetermined attaching surface is a surface inclined by 0 to 60 degrees with respect to a horizontal plane.

4. The pressure detector according to claim 3, wherein the inlet port extends in a direction tangent to the liquid-phase portion in plan view in such a manner as to generate a vortex with the liquid flowing into the liquid-phase portion from the inlet opening.

5. The pressure detector according to claim 4, wherein the case includes a liquid-phase-portion case defining the liquid-phase portion, and a gas-phase-portion case defining the gas-phase portion; the membrane member is held between the liquid-phase-portion case and the gas-phase-portion case that are mated to each other; and the inlet port extends substantially parallel to an attaching plane defined for the membrane member while the outlet port extends at a predetermined angle with respect to the attaching plane defined for the membrane member.

6. The pressure detector according to claim 3, wherein the predetermined attaching surface is inclined at an angle of about 35 degrees with respect to the horizontal plane.

7. The pressure detector according to claim 1, wherein the inlet port extends in a direction tangent to the liquid-phase portion in plan view in such a manner as to generate a vortex with the liquid flowing into the liquid-phase portion from the inlet opening.

8. A blood circuit to which the pressure detector according to claim 1 is connected.

9. The pressure detector according to claim 1, wherein the inlet port extends parallel to the attaching plane of the membrane member so that liquid introduced into the liquid-phase-portion extends parallel the attaching plane.

10. The pressure detector according to claim 9, wherein the inlet port extends in a direction tangent to the liquid-phase portion in plan view in such a manner as to generate a vortex with the liquid flowing into the liquid-phase portion from the inlet opening.

11. The pressure detector according claim 9, wherein the attaching plane is a plane the membrane member extends along when the membrane member is not being displaced.

\* \* \* \* \*